United States Patent
De Baerdemaeker et al.

(10) Patent No.: US 6,722,201 B2
(45) Date of Patent: Apr. 20, 2004

(54) METHOD AND DEVICE FOR DETERMINING VIBRATION CHARACTERISTICS OF VIBRATED ARTICLES SUCH AS EGGS

(75) Inventors: Josse De Baerdemaeker, Heverlee (BE); Peter Coucke, Heverlee (BE); Gerrit Hout, Barneveld (NL); Bart De Ketelaere, Heverlee (BE); Adrianus van Pinxteren, Eemnes (NL); Willem van Veldhuisen, Barneveld (NL)

(73) Assignee: FPS Food Processing Systems B.V. (NL)

( * ) Notice: Subject to any disclaimer, the term of this patent is extended or adjusted under 35 U.S.C. 154(b) by 0 days.

(21) Appl. No.: 10/090,006

(22) Filed: Mar. 5, 2002

(65) Prior Publication Data

US 2002/0189321 A1 Dec. 19, 2002

(30) Foreign Application Priority Data

Mar. 5, 2001 (EP) .............................................. 01200783

(51) Int. Cl.$^7$ .............................................. G01N 29/04
(52) U.S. Cl. ........................... 73/627; 73/12.12; 73/575
(58) Field of Search ....................... 73/627, 629, 12.12, 73/575, 11.09, 584, 587, 595, 11.01, 11.03, 12.06, 12.02, 579, 597, 598, 599, 600, 602

(56) References Cited

U.S. PATENT DOCUMENTS

| | | | |
|---|---|---|---|
| 3,067,605 A | | 12/1962 | Bliss |
| 3,744,299 A | | 7/1973 | Bliss ........................... 73/595 |
| 5,131,274 A | * | 7/1992 | Schouenborg ............... 73/595 |
| 5,426,977 A | * | 6/1995 | Johnston et al. ............... 73/595 |
| 5,490,437 A | * | 2/1996 | Hebert et al. ................... 81/22 |
| 5,696,325 A | * | 12/1997 | Coucke et al. ................. 73/595 |
| 5,728,939 A | * | 3/1998 | Moayeri ..................... 73/595 |
| 5,760,691 A | * | 6/1998 | Egli ........................ 340/573.6 |
| 6,089,079 A | * | 7/2000 | Rosenblum et al. ........... 73/73 |

FOREIGN PATENT DOCUMENTS

| | | |
|---|---|---|
| EP | 0 738 888 | 11/2001 |
| JP | 10-227766 | 8/1998 |
| NL | 9401388 | 4/1996 |

OTHER PUBLICATIONS

"Assessment of some physical quality parameters of eggs based on vibration analysis", P. Coucke, Catholic University Leuven, Mar. 1998.

"Non–destructive firmness measurements of apples", Armstrong et al., Am. Soc. Agr. Eng., Jun. 1992.

* cited by examiner

*Primary Examiner*—Hezron Williams
*Assistant Examiner*—Jacques Saint-Surin
(74) *Attorney, Agent, or Firm*—Stites & Harbison PLLC; Marvin Petry

(57) ABSTRACT

This invention relates to a device for determining vibration characteristics of vibrated, supported, generally round, substantially ellipsoid articles, such as eggs, comprising:

an elastic hammer with handle and head, for tapping and thereby acoustically vibrating such article, a handle drive element for reciprocating the hammer generally in a plane around an axis in the handle, a microphone arranged immediately adjacent to and directed to the article, for picking up acoustic vibrations generated by the article, and a signal processing means for processing the signals picked up by the microphone for determining vibration characteristics of the article, characterized in that the handle adjacent the axis consists of an arm portion to be driven which is connected, through a hinge element, with a handle end having at the extremity thereof a mount having therein a ball as a head, while at least the hinge element and the handle end form a hammer rod in one piece.

With great advantage, sorting machines of fruit or eggs can be equipped with such devices to determine firmness, or fracture, respectively, and to sort them accordingly.

17 Claims, 4 Drawing Sheets

METHOD AND DEVICE FOR DETERMINING VIBRATION CHARACTERISTICS OF VIBRATED ARTICLES SUCH AS EGGS

The present invention relates to a device for determining vibration characteristics of vibrated, supported, generally round, substantially ellipsoid articles, such as eggs, comprising:
- a hammer with a handle and head, for tapping and thereby acoustically vibrating such article,
- a handle driving element for reciprocating the hammer generally in a plane around an axis in the handle,
- a microphone arranged immediately adjacent to and directed to the article, for picking up acoustic vibrations generated by the article, and
- a signal processing means for processing the signals picked up by the microphone for determining vibration characteristics of the article.

Such devices have long been known. In U.S. Pat. No. 3,067,605 a tapping device for determining cracks and fractures in the egg shell are described, with which in particular the extent of rebound after tapping is determined. In NL9401388, by tapping an egg, for instance by means of a ball falling onto it, the egg's reaction thereto, in particular the acoustic resonance, is measured with a microphone arranged nearby. In "Assessment of some physical quality parameters of eggs based on vibration analysis", P. Coucke, Catholic University Leuven, March 1998, an extensive analysis is shown both of publications from the past and of measurements on resonance modes, with which well-defined features and characteristics of eggs can be traced. In JP10227766 a tapping device for eggs is described, wherein the tapping rod consists of two parts connected by a spiral spring, whilst the reciprocating movement involves an interplay between pushing around by a stop and a rebounding of a supporting spring.

Also for determining the properties of fruits, in particular determining the firmness of apples from the acoustic resonance thereof, for instance described in "Non-destructive firmness measurements of apples", Armstrong et al., Am. Soc. Agr. Eng., June 1992, the principle of tapping with a hammer and picking up the sound signals with a microphone is applied.

All of these examples show that solutions are being sought to the problem of effecting resonances in a manner as uniform as possible, and subsequently measuring thus generated signals in a manner as accurate as possible. An important problem is formed by the tapping itself. It has been demonstrated that in many cases tapping is a repetitive phenomenon, to be qualified as bouncing. This is used, for instance, in EP738888, also in applicant's name. In this document, essentially the reaction of impact on the tapping element itself is examined. If any resonances can be measured there at all, these will often be disturbed by the repetitive tap mentioned.

The present invention has resulted in a device which contemplates a further improvement and is characterized in that the handle adjacent the axis consists of an arm portion to be driven which is connected, through a hinge element, with a handle end having at the extremity thereof a mount having therein a ball as a head, while at least the hinge element and the handle end form a hammer rod in one piece.

It has been found that, with this, a single tapping pulse is obtained. Such a pulse is very suitable for further signal processing, in particular for determining the frequency spectrum associated with such a pulse. Such a spectrum contains all possible information about the resonance modes which, as a result of tapping, are generated by the tapped articles.

In further embodiments of the present invention, the device is characterized in that the plane passes through the long axis of the article, that at least a single microphone is arranged in said plane, or through the long axis in a second plane, substantially perpendicular to said plane.

Another embodiment of the device according to the invention is characterized in that the hammer rod and the arm portion constitute one whole, with the hammer rod forming a leaf spring portion having a spring constant k between 1.2 and 1.6 N/m. The pulses herewith obtained are very suitable and short, and thus result in a corresponding, highly suitable frequency spectrum.

In a particular embodiment of the invention, the device is characterized in that the handle driving element further comprises a holder with pin hole for a pin perpendicular to the first plane and through the arm portion, with an electromagnet attached to the holder for reciprocating the hammer generally in said plane, with a magnet included in the arm portion adjacent the electromagnet, and with a stop element for the arm portion during the forward movement.

In a further particular embodiment, the device is characterized in that the handle driving element further comprises a stop for interrupting the return movement of the hammer, and in a still further embodiment that the ball is made of steel, and that the handle driving element further comprises a holding element with which the hammer is held after a return movement, the holding element consisting of a stop block for the leaf spring portion and a holding magnet for the ball.

In a still further embodiment, the device is characterized in that the hammer rod is further coupled with the arm portion by means of a bistable switch, the switch having a first and a second snap position, while the hammer rod is movable either into the first snap position or into the second snap position. In this way, it is suitably ensured that the hammer, after tapping, is immediately retracted and remains retracted, and bouncing is thereby avoided.

In a particular embodiment, the device is characterized in that the hammer rod in the forward movement is switched to the first snap position, and in the return movement is switched to the second snap position.

With such a device, the manner of tapping can be set very accurately. Especially in sorting large numbers of articles varying slightly in shape, this is highly advantageous, and very reliable results are obtained.

Further, the invention comprises a method for determining vibration characteristics of vibrated articles such as eggs, characterized in that the tapping of the articles is performed with the above-mentioned device, in particular characterized in that tapping consists in a single momentary tapping pulse.

According to a further elaboration of the present method, it is used in a sorting device for eggs, wherein in particular the eggs are tapped at least twice. In a highly suitable manner, thus a suitable sorting criterion is created.

Hereinafter, the invention will be elucidated in more detail with reference to the accompanying drawing, wherein.

Figure 4A:
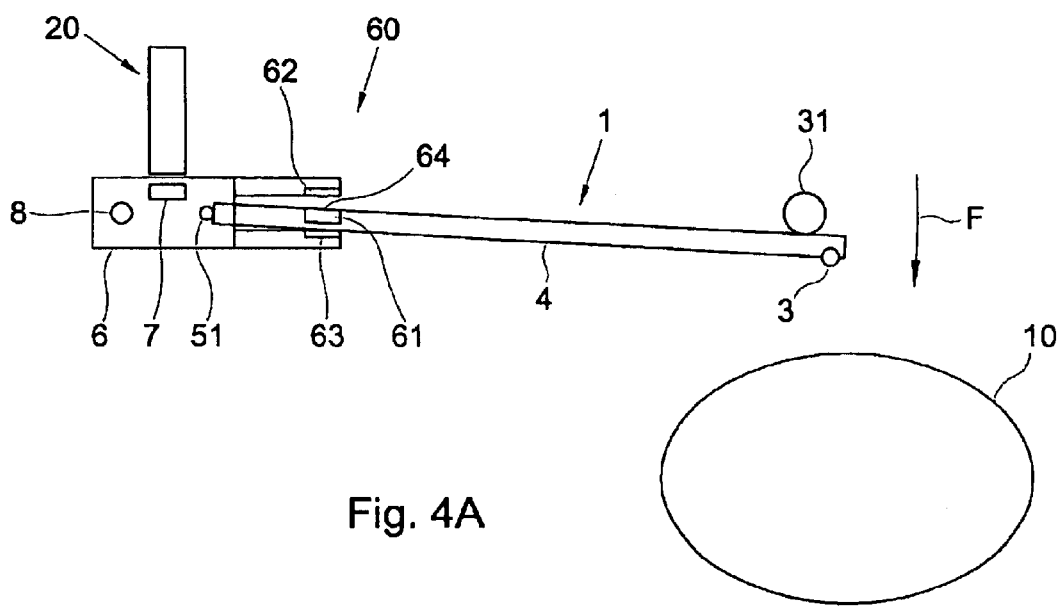
Figure 4B:
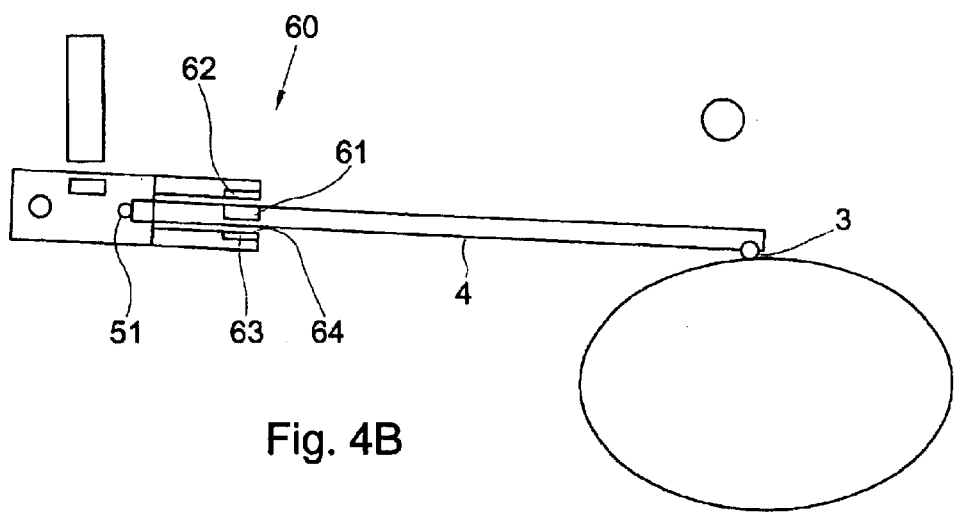
Figure 4C:
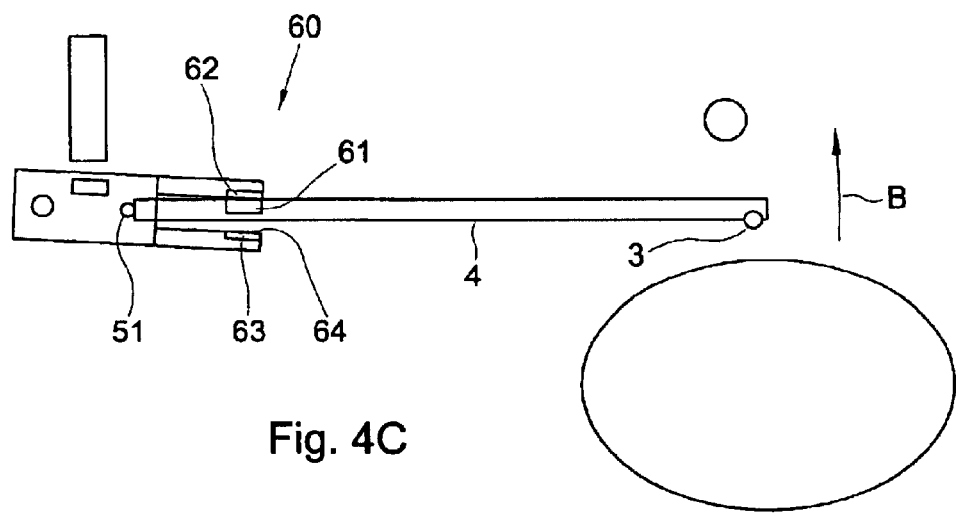
Figure 5A:
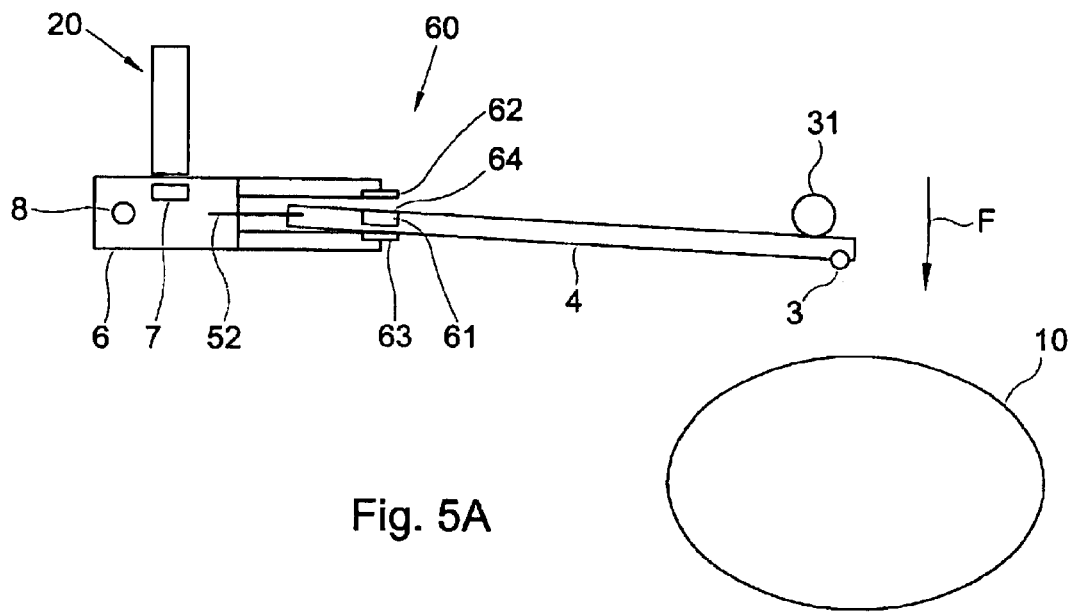
Figure 5B:
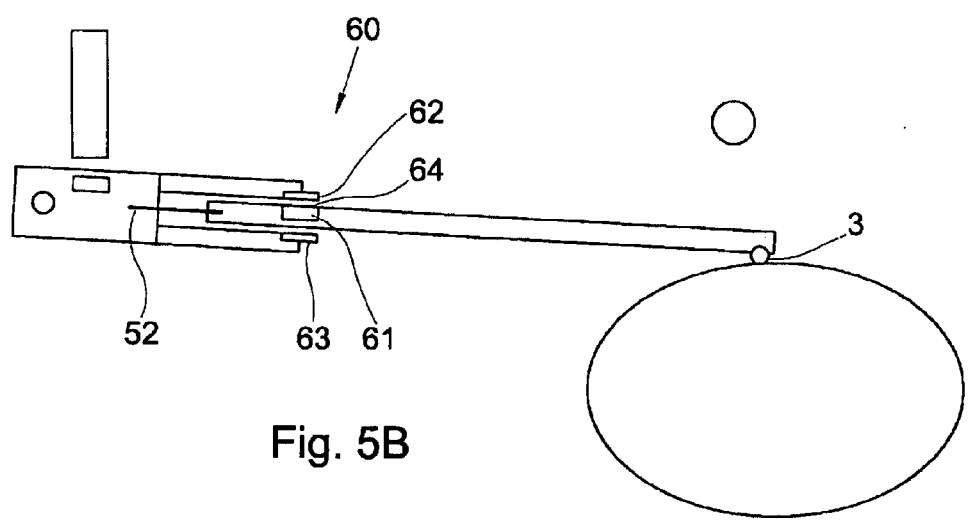
Figure 5C:
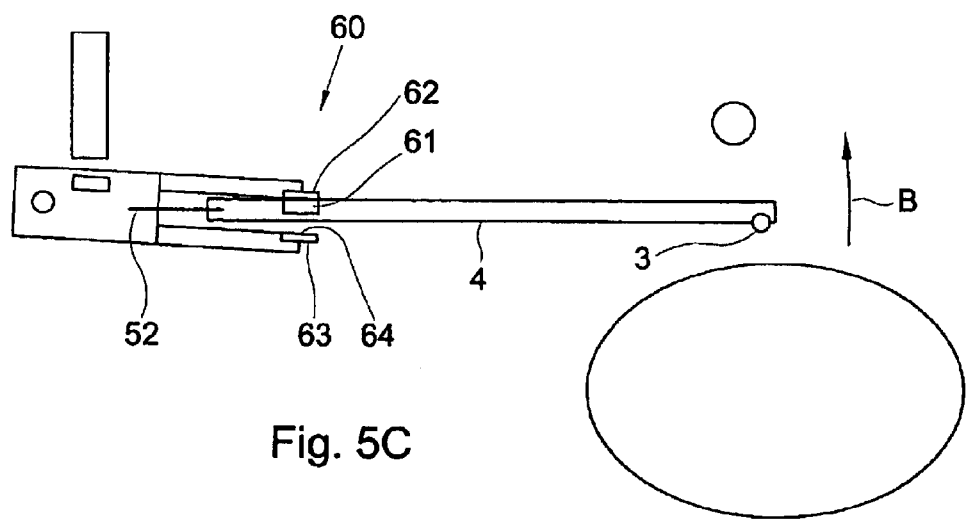

FIGS. 4A, 4B, and 4C are schematic elevations of a second exemplary embodiment according to the present invention; and FIGS. 5A, 5B, and 5C present schematic elevations of a third exemplary embodiment according to the present invention.

In the different figures, corresponding parts are indicated in the same manner.

Figure 1:
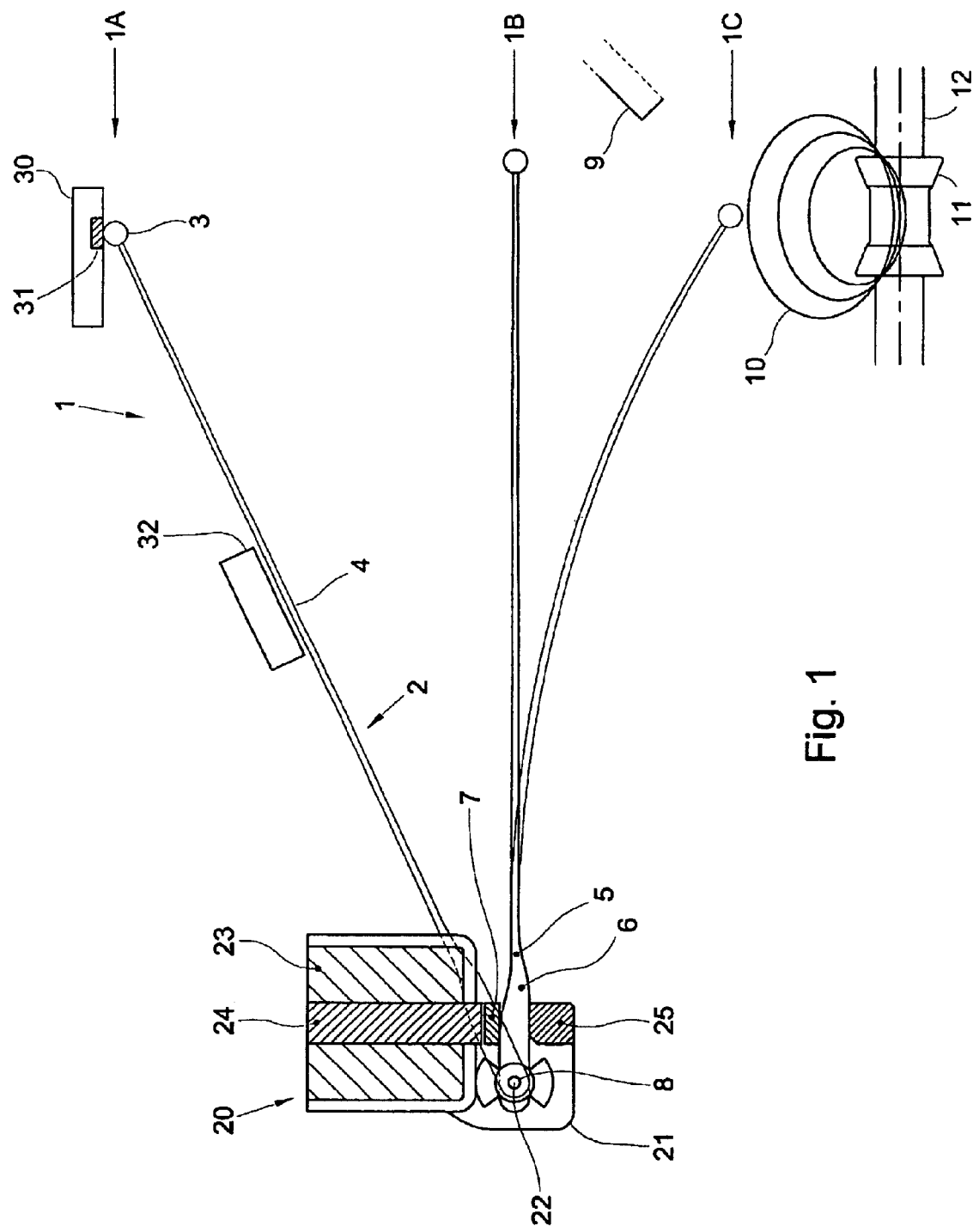
FIG. 1 shows an elevation of an exemplary embodiment of the device according to the present invention.

In FIG. 1 the device for tapping comprises a hammer 1, with handle 2 and head 3, for instance a small steel ball framed in the end thereof. The hammer with handle and head preferably constitute one whole and are manufactured from a well-selected plastic. More particularly, the handle consists of a handle end 4 which is connected through a hinge element 5 with an arm portion 6, having a magnet 7 arranged therein. At the end of the arm portion 6, a pin 8 is arranged allowing the hammer to rotate. Hinge element 5 and handle end 4 constitute a hammer rod in one piece. Advantageously, arm portion and hammer rod form one whole, with the hammer rod forming a leaf spring portion having a spring constant k between 1.2 and 1.6 N/m.

The pin 8 fits into a pin hole 22 of a holder 21 of handle driving element 20. An electromagnet 23 with core 24 is fixedly connected with this holder 21.

Further, in this figure, it can be seen how the leaf spring portion during the "forward" movement can bend so that the ball 3 just taps an egg 10 disposed on a support 11, more particularly between two rollers or hourglass-shaped rollers jointly forming a nest, mounted on a shaft 12, associated with a conveyor of an egg sorting device. With a microphone 9, the acoustic vibrations resulting from tapping can be picked up.

Although this sorting device is not further shown, it will be clear that the eggs disposed on rollers 11 are passed under these hammers 1 to be tapped during transport. The further features to be determined can be used for sorting further downstream in the sorting device. As described for eggs by P. Coucke (see supra), for instance the S20, S30, and S40 resonance modes can be observed. The shape of such a resonance signal, for instance of the amplitude, or also of the frequency spectrum, contains information about the condition of the egg shell, i.e. yes/no fracture or crack, egg shell strength, or also information about the contents of the egg.

In particular, the hammer is represented in three positions, viz. in rest position 1A, in central position 1B, and in tapping position 1C. In its rest position, the hammer rests against a holding element, consisting of a holder block 30 with holder magnet 31, and a stop block 32. With reference to these positions, the operation can be elucidated as follows. From its rest position 1A, after excitation of the electromagnet 23, the hammer 1, through its arm portion 6 having therein magnet 7, is forced to move downwards, to be seen as the "forward" movement. In position 1B the arm portion 6 butts against a stop 25 which is arranged on the holder 21. The device of the invention according to this exemplary embodiment, in particular with the handle end 4, makes it possible for this handle end with the ball 3 to bend or swing so far that the ball just taps the egg 10, as indicated in tapping position 1C. The pulse which is thus administered is very short in duration, also referred to as Dirac pulse. In this way, a very suitable acoustic vibration signal is obtained, to be transformed into a broad frequency spectrum through application of Fourier analysis, in particular using so-called FFT, i.e. Fast Fourier Transform.

The energization can now be set such that during the return or backward movement, the arm portion is momentarily attracted and the hammer will be retained by the holding element. The ball will then cling to holder magnet 31, while any further bending will be prevented by stop block 32.

For eggs of different sizes, as schematically indicated in FIG. 4, the excitation of the electromagnet 23, and hence the stroke of the reciprocating movement of the hammer 1, can be adjusted and controlled, for instance by first measuring the size, and then using this signal for the purpose of excitation. Advantageously, the whole hammer can be manufactured from the same plastic, for instance through injection molding. Depending on the type of article, the back-and-forth movement can also take place in a direction other than the vertical direction.

Figure 2:
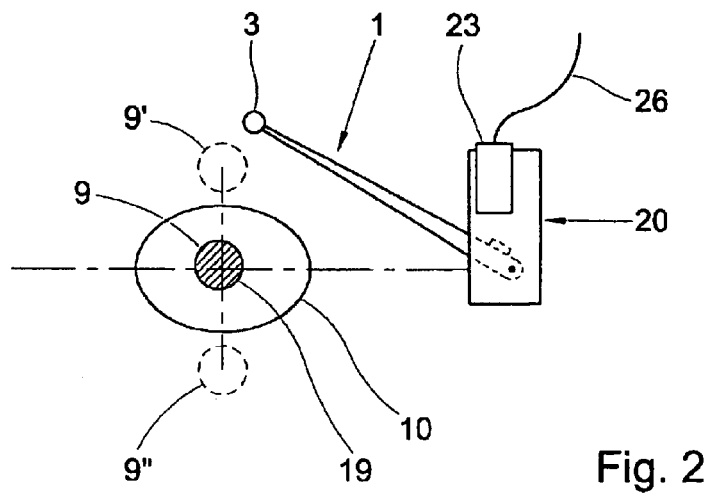
FIG. 2 shows a schematic elevation of the situation according to FIG. 1 concerning another aspect of the invention.

FIG. 2 schematically represents a situation similar to that in FIG. 1. In the embodiment according to the present invention, it is advantageous to have the reciprocating movement of the hammer 1 take place approximately in a vertical plane, with microphone 9 disposed approximately in the "equator" plane, i.e. the plane perpendicular to said vertical plane and likewise passing through the long axis of the article, such as an egg 10 here. Also eligible are positions 9' or 9", in the same vertical plane through the long axis of the article, depending on the space left clear next to the hammer 1. When a single or more microphones are arranged in the equator plane, it is precisely the resonance modes in this plane that will be well observable upon tapping. Further, in this figure, two signal lines are indicated, line 19 for the microphone and line 26 for the electromagnet 23, respectively leading to a signal processing device, not shown, and a control device, not shown either.

Figure 3:
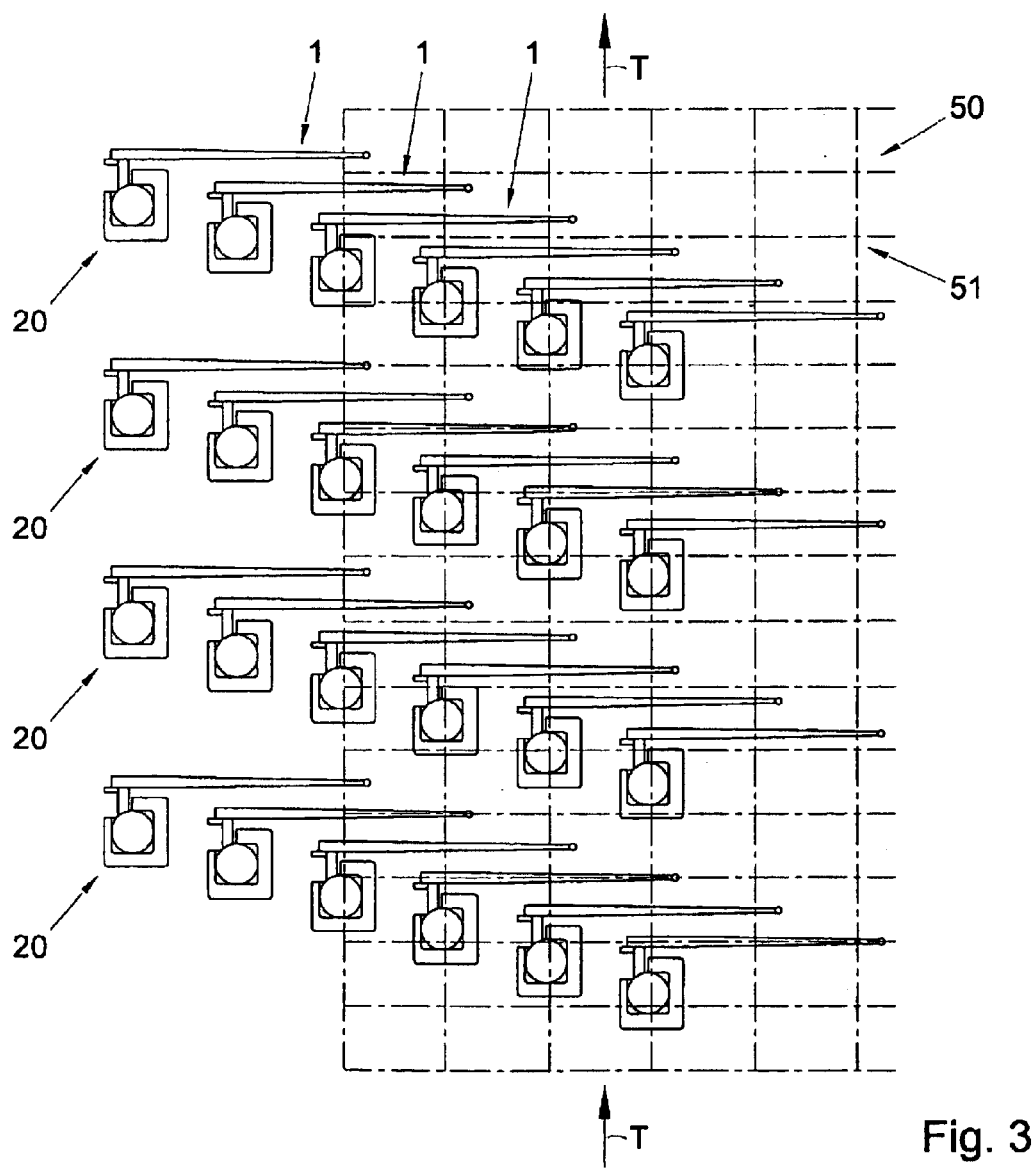
FIG. 3 shows an elevation of a sorting line where the devices according to the invention are used.

In FIG. 3, a top plan view of a part of a sorting device 50 is represented, with the positions of the articles, for instance eggs, schematically represented as the intersections 51 of the chain-dotted lines. The transport direction of the sorting device is designated by arrow T. Also indicated are hammers 1 and handle driving elements 20. In order to tap the eggs several times, the hammers are so arranged that in the example shown, each egg can be tapped four times, without the hammers being in each other's way.

In FIGS. 4A, 4B and 4C, a second exemplary embodiment according to the invention is shown, in which the arm portion 6 and the handle end 4 are mutually connected through a hinge element 51, for instance a separate pin, or also a joint in which the pin, handle end and arm portion are formed as one whole, for instance through injection molding of a suitable plastic. In the figures, a bistable switch 60 is indicated, consisting in particular of a magnet 61 in the part of the handle end located adjacent the arm portion, as well as two magnets 62 and 63, located at some distance therefrom, in the arm portion 6, with an interspace 64, whilst the handle end clings either to one magnet 62 or to the other magnet 63, which positions constitute snap positions for this handle end.

Upon excitation of the electromagnet, the arm portion in the plane referred to will start the forward movement towards the egg 10 represented here, indicated with an arrow F, with the handle end snapped by magnet 63, shown in FIG. 4A. At the moment of tapping, represented in FIG. 4B, the hinge element 51 will allow the handle end to snap from one snap position to the other, the handle end now clinging to magnet 62, whereby the tapping pulse is shortened with great advantage and bouncing is avoided. Ideally, this will take place precisely during the tapping pulse. The forward or backward movement is shown in FIG. 4C and indicated with an arrow B, whereby the hammer returns to the starting position and the ball 3 clings to holder magnet 31 again. During the movement in the direction of F, an additional contribution to this movement can be made by suitably exciting the electromagnet in the holder 20.

To anyone skilled in the art, it will be clear that here too the materials can be suitably selected to thereby improve elasticity. Less elastic materials may even suffice, because the bistable switch will prevent bouncing in an advantageous manner.

In FIGS. 5A, 5B and 5C, a third embodiment is shown. Here, the hinge element is a leaf spring 52. The operation is otherwise entirely comparable to that of the embodiment according to FIG. 4.

To those skilled in the art, it will be clear that other types of adhering elements and bistable switches can be used, such as, respectively, springs without adhering elements, or also in combination with electromagnets.

EXAMPLE

To limit fracture and wear of the hammers as much as possible, the dimensions have been selected such that upon bending, the tension in the leaf spring is equally high throughout, with the moment decreasing linearly from the arm portion, and being 0 Nm at the terminal end. Experiments have been performed with hammers of the following specifications:

| | |
|---|---|
| plastic | PBT (polybutylene terephthalate) |
| angle between 1A and 1B | 24° |
| center-to-center distance axis-ball | 198 mm |
| length of arm portion | 40 mm |
| ball diameter | 4.5 mm |
| density ball (steel) | 7.8 kg/m$^3$ |
| tapping pulse duration | 0.5 ms |
| tapping speed | 1.5 m/second |
| thickness of end of leaf spring | 0.9 mm |
| thickness of beginning of leaf spring | 1.2 mm |
| width of end of leaf spring | 4 mm |
| width of beginning of leaf spring | 8 mm |

It will be clear to anyone skilled in the art that small changes in the choice of the components, materials, distances and dimensioning fall within the scope of protection of the appended claims. For instance, other energization means than electromagnetic ones can be used. Also, the pin and hole therefor can be changed around. Further, energization and signal implementation will be carried out in a known manner.

What is claimed is:

1. A device for determining vibration characteristics of substantially ellipsoid articles, said device comprising:
    an elastic hammer with a handle having an arm portion, a hinge element and a handle with a ball head, said ball, said hinge element and handle end forming a hammer rod head for tapping and thereby acoustically vibrating the article;
    a handle driving element for reciprocating the hammer generally in a plane around an axis passing through the handle adjacent the arm portion;
    a microphone arranged adjacent to and directed to the article, to pick up acoustic vibrations generated by the article; and
    a signal processor for processing the signals picked up by the microphone for determining vibration characteristics of the article.

2. The device according to claim 1, wherein the plane passes through the long axis of the article.

3. The device according to claim 1, wherein at least a single microphone is arranged in said plane, or through the long axis in a second plane substantially perpendicular to said plane.

4. The device according to claim 1, wherein the hammer rod and the arm portion form a whole, with the hammer rod forming a leaf spring portion having a spring constant k in the range between 1.2 and 1.6 N/m.

5. The device according to claim 1, wherein the handle driving element further comprises a holder with pin hole for a pin perpendicular to the first plane and through the arm portion, with an electromagnet attached to the holder for reciprocating the hammer generally in said plane, with the magnet included in the arm portion adjacent the electromagnet, and with a stop element for the arm portion during the forward movement.

6. The device according to claim 5, wherein the handle driving element further comprises a stop for interrupting the backward movement of the hammer.

7. The device according to claim 5, wherein the ball is made of steel, and the handle driving element further comprises a holding element with which the hammer is held after a backward movement, the holder element consisting of a stop block for the leaf spring portion and a holding magnet for the ball.

8. The device according to claim 1, wherein the hammer rod is further coupled by means of a bistable switch with the arm portion, the switch having a first and a second snap position, and the hammer rod being movable either to the first snap position or the second snap position.

9. The device according to claim 8, wherein the hammer rod in the forward movement is switched to the first snap position, and in the backward movement to the second snap position.

10. The device according to claim 1, wherein the hinge element connection between the arm portion and the handle end is such that upon excitation of the handle driving element, a single tapping pulse is obtained.

11. A method for determining vibration characteristics of vibrated articles, said method comprising:
    tapping articles using a device according to claim 1.

12. The method according to claim 11, wherein said tapping consists of a single momentary tapping pulse.

13. The method according to claim 11, wherein said method is used in a device for sorting eggs.

14. The method according to claim 11, wherein the articles are tapped at least twice.

15. A device for determining vibration characteristics of substantially ellipsoid articles, said device comprising:
    an elastic hammer with a handle having an arm portion, a hinge element and a handle with a ball head, said ball, said hinge element and handle end forming a hammer rod head for tapping and thereby acoustically vibrating the article;
    a handle driving element for reciprocating the hammer generally in a plane around an axis passing through the handle adjacent the arm portion, said handle driving element comprising a holder with pin hole for a pin perpendicular to the first plane and through the arm portion, with an electromagnet attached to the holder for reciprocating the hammer generally in said plane, with the magnet included in the arm portion adjacent the electromagnet, and with a stop element for the arm portion during the forward movement;
    a microphone arranged adjacent to and directed to the article, to pick up acoustic vibrations generated by the article; and
    a signal processor for processing the signals picked up by the microphone for determining vibration characteristics of the article.

16. The device according to claim 15, wherein the handle driving element further comprises a stop for interrupting the backward movement of the hammer.

17. The device according to claim 15, wherein the ball is made of steel, and the handle driving element further comprises a holding element with which the hammer is held after a backward movement, the holder element consisting of a stop block for the leaf spring portion and a holding magnet for the ball.

* * * * *